United States Patent [19]
Cormier

[11] Patent Number: 5,300,142
[45] Date of Patent: Apr. 5, 1994

[54] COMPOSITIONS AND PROCESS FOR HIGHLIGHTING SURFACE DEFECTS IN, AND PREVENTION OF ADHESION OF HOT METAL TO, METAL SURFACES

[75] Inventor: Gerald J. Cormier, Troy, Mich.

[73] Assignee: Henkel Corporation, Plymouth Meeting, Pa.

[21] Appl. No.: 49,695

[22] Filed: Apr. 16, 1993

Related U.S. Application Data

[63] Continuation-in-part of Ser. No. 928,927, Aug. 11, 1992, abandoned.

[51] Int. Cl.$^5$ .................... C09D 5/00; C09D 129/02
[52] U.S. Cl. .................... 106/14.14; 106/14.13; 106/287.24
[58] Field of Search .................... 106/14.14, 2, 287.24, 106/14.13

[56] References Cited

U.S. PATENT DOCUMENTS 5,131,948  7/1992  Higashiyama et al. .......... 106/14.14

*Primary Examiner*—David Brunsman
*Attorney, Agent, or Firm*—Ernest G. Szoke; Wayne C. Jaeschke; Norvell E. Wisdom, Jr.

[57] ABSTRACT

An aqueous liquid composition containing polyethylene glycol with a molecular weight in the range of about 200 to about 8000, nonionic surfactant, and a corrosion inhibitor, and optionally, amphoteric surfactants and fluorinated surfactants is useful as a highlighting liquid for detection of surface irregularities on shaped metal surfaces and for preventing adhesion of weld splatter on surfaces coated with the composition. Preferably the corrosion inhibitor includes alkali metal salts of boric acid and of a mixture of branched chain carboxylic acids and amino acids.

15 Claims, No Drawings

COMPOSITIONS AND PROCESS FOR HIGHLIGHTING SURFACE DEFECTS IN, AND PREVENTION OF ADHESION OF HOT METAL TO, METAL SURFACES

CROSS-REFERENCE TO RELATED APPLICATION

This application is a continuation-in-part of copending application Ser. No. 928,927 filed Aug. 11, 1992, now abandoned.

FIELD OF THE INVENTION

This invention relates to an aqueous composition that is substantially free from volatile organic compounds ("VOC") and is useful for at least one, and in some embodiments for both, of two purposes in connection with industrial metal working, particularly in the automotive industry: providing a glossy surface to facilitate the visual detection of small scale surface shape irregularities, commonly called "dents" and "dings", in shaped metal surfaces that are intended eventually to have a glossy finish, but have not yet reached that stage of their processing, and inhibiting the adhesion of small amounts of hot metal, commonly called "weld splatter", on nearby surfaces during welding of metal objects.

BACKGROUND OF THE INVENTION AND RELATED ART

During industrial manufacturing of many types of metal goods, it is common practice to weld together two or more separate pieces of metal to form a unitary structure. Normally, welding is confined to a relatively narrow zone of the total structure formed by welding, but it produces small and very hot, often molten, bits of metal that are discharged into the space surrounding the welding zone and often come into contact with and, unless inhibited from doing so, stick to, nearby areas of the structure being formed by welding. Any such weld splatter adhering to the structure being formed by welding becomes a surface defect, and, if the surface of the structure being welded is intended eventually to become a glossy finished surface, such as an automobile body, file cabinet, or the like, any such defects must be prevented or repaired in order to achieve a satisfactory finish. Repairing defects of this type is relatively expensive, so that prevention is highly preferred.

The adhesion of welding splatter can be inhibited by covering surfaces in the vicinity of welds with an inhibiting composition. Compositions now in commercial use for this purpose are believed to consist primarily of water, alkali neutralized complex acrylic acids, high foaming nonionic surfactants, and defoamers. These materials are often not fully satisfactory for at least two reasons: They have sufficiently high viscosity to develop noticeable thickness variation ("sagging") on non-horizontal surfaces, and they offer insufficient protection against corrosion when surfaces coated with them are stored for more than a day or two.

During the manufacture of automobiles and other metal goods with decorative glossy surfaces, it is common practice to inspect Class A surfaces for metal surface shape irregularities (dents or dings) prior to painting the surfaces; this inspection and/or the technique used in it is commonly referred to as "hiliting" or "highlighting". Detecting and correcting a metal defect prior to painting simplifies the painting operation and precludes the need for subsequent removal of paint to repair the defect and repainting of the surface. Repairing the defect and repainting results in higher costs for time, materials and labor while reducing product quality.

During automotive assembly operations, bare metal panels such as doors, fenders, roofs, quarter panels, and the like are attached to the frame of the vehicle. The vehicle is then cleaned to remove oil and dirt as well as any grinding dust. The clean metal has a dull finish which makes it difficult to see minor dents and dings in the metal panels of the vehicle.

In practice, metal parts to be painted, especially sheet metal parts of an auto body, are first assembled into a subassembly. The subassembly is then cleaned to remove oxidation, oil, and any other contaminants on the surface to be painted. The cleaned subassembly is then coated with the hilite composition and inspected. A hilite material is applied to the vehicle either by hand wiping or by a mechanical device, typically a number of rotating brushes that have been wetted with a hilite solution. Excess hilite solution is permitted to drain for a short period and the resulting glossy surface of the vehicle is inspected for dents and dings. Any dents and dings found are marked for repair and then lightly sanded and/or bumped out as needed.

The subassembly after hilite inspection and repair, if necessary, is then treated to remove the hilite material. A protective coating such as a phosphate conversion coating is applied to the metal and the metal is then coated with a decorative and protective organic coating.

To be optimally useful, a hilite composition must rapidly form a glossy, foam free coating on the metal surface, must not stain or etch the metal, and must be readily removable from the metal.

Frequently, inspection of the partially assembled vehicles is not performed immediately after application of the hilite solution because of floor space restrictions, lunch breaks, line stoppages, weekend down time, or the like. Such delays impose major performance requirements on the hilite composition. During any delay from application of the hilite composition to inspection, the gloss of the treated surface should not change visually due to drying; the retained hilite solution must not etch or stain the metal surface or otherwise make the surface unsuitable for painting; and the retained hilite solution should provide some corrosion protection to the metal. (An unprotected metal surface, particularly one of zinc alloy coated steel, aluminum, or cold rolled steel, will very quickly rust or otherwise oxidize.)

Currently available hilite compositions normally contain solvents such as kerosene or mineral spirits or water soluble solvents such as glycol ethers. The compositions also contain surfactants, typically nonionics, and corrosion inhibitors such as petroleum sulphonates, triethanolamines or sodium nitrite. The commercially available hilite compositions provide a temporarily glossy surface and short term corrosion protection. The solvents used in the presently available formulations are volatile. Kerosene and mineral spirits evaporate much more rapidly than glycol ethers, but even glycol ethers are considered to be VOC for pollution control purposes, so that these compositions must be used in compliance with government regulations and restrictions for VOC use. (See ASTM 2369, "Volatile Content of Coatings".) Avoidance of this problem is one object of the present invention.

DESCRIPTION OF THE INVENTION

Other than in the operating examples and claims, or where otherwise expressly indicated, all numbers expressing conditions of use or quantities of ingredients used herein are to be understood as modified in all instances by the term "about" in describing the broadest aspects of the invention. Practice within the exact numerical limits given is generally preferred, however. Also, unless expressly stated to the contrary: the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; specification of materials in ionic form implies the presence of sufficient counterions to produce electrical neutrality for the composition as a whole; and any counterions thus implicitly specified should preferably be selected from among other constituents explicitly specified in ionic form, to the extent possible; otherwise such counterions may be freely selected, except for avoiding counterions that act adversely to the stated purposes of the invention.

SUMMARY OF THE INVENTION

One major embodiment of the present invention is a composition comprising polyethylene glycol, surfactant, corrosion inhibitor, and other optional additives that can provide a water based solution which forms a film on a metal surface suitable for the detection of imperfections on the metal surface and/or for inhibition of adhesion of bits of hot metal deposited on the surface.

More specifically, a composition of one embodiment of the invention comprises, preferably consists essentially of, or most preferably consists of, water and:
(A) from 1.0 to 60% by weight of polyethylene glycol having a weight average molecular weight in the range from 200 to 500:
(B) from 0.5 to 15.0% by weight total of low foaming nonionic and/or nonstaining anionic surfactant, preferably free from fluorine;
(C) a corrosion inhibiting amount of corrosion inhibitor; and, optionally, one or more of:
(D) from 0.3 to 10% by weight total of low foaming amphoteric surfactant, preferably free from fluorine;
(E) from 0.001 to 2% by weight of a low or moderate foaming fluorosurfactant ("fluorosurfactant" is used herein to mean any surfactant containing at least one fluorine atom per molecule);
(F) 0 to 1% by weight of a rheology modifying agent; and
(G) 0 to 59% by weight of polyethylene glycol having a weight average molecular weight of 600 or higher, preferably from 1000 to 10,000, or more preferably from 4,000 to 8,000, except that the total of components (A) and (G) should not exceed 60% by weight.

As used herein, the term "low foaming surfactant" denotes a surfactant which produces less than 60/30 mm of foam according to the shaking test method described below, while the term "moderate foaming surfactant" denotes a surfactant which produces more than 60/30 but less than 100/60 mm of foam according to the same shaking test method.

SHAKING TEST METHOD

A glass stoppered 250 milliliter measuring cylinder, about 30 millimeters in diameter, is filled to the 150 milliliter mark with a 0.1% by weight solution in water at room temperature of the surfactant to be tested. The measuring cylinder is stoppered and then vigorously shaken for 30 seconds. The foam height immediately after shaking is measured, and the foam height is measured again 30 seconds after shaking is completed. A foam height of 60 millimeters or less after shaking or 30 millimeters or less 30 seconds after shaking indicates a low foam surfactant. A foam height that does not indicate a low foam surfactant but is not more than 100 millimeters immediately after shaking or not more than 60 millimeters 30 seconds after shaking indicates a moderate foaming surfactant.

A composition of the invention can be provided as a concentrate for dilution before use or can be provided as a ready to use composition. Generally, compositions of the invention at working concentration contain from 85 to 50% by weight of water. A dilutable concentrate generally contains from 10% to 60% by weight of water. A dilutable concentrate preferably contains a sufficient amount of water to form a homogenous single phase mixture. Other embodiments of the invention include a process of using a composition according to the invention for a highlighting inspection or to inhibit adhesion of bits of hot metal to surfaces coated with the composition.

DESCRIPTION OF PREFERRED EMBODIMENTS

The metal surfaces treated according to this invention are preferably selected from the group consisting of cold rolled steel, hot-dip and electrogalvanized steel, other zinc alloy coated steels, zinc and its alloys that contain at least 80 atomic % of zinc, aluminum, and aluminum alloys that contain at least 45 atomic percent of aluminum.

When a composition according to this invention is to be used for highlighting, optional component (G) is preferably omitted or kept to a very low amount, because it decreases the gloss obtained with the composition. However, for inhibition of adhesion of weld splatter, optional component (G) is preferably included in most cases, because it provides a mechanically tougher film that offers better protection against corrosion during short term storage. Also, when a composition according to this invention is to be used for highlighting, component (D) is preferably included in order to guard against any loss of gloss because of phase separation. When the composition is to be used for weld splatter adhesion inhibition, however, component (D) is less important although not at all harmful.

Polyethylene glycols sold by Dow Chemical Company under the trade name of POLYGLYCOL E and by BASF under the trade name PLURACOL are useful in the practice of the invention. Polyethylene glycols have the formula:

and those where n on average is in the range of about 4 to about 11 are useful for component (A) of a composition according to the invention. In the commercially available polyethyleneglycols the trade name is usually followed by a number which corresponds to the average molecular weight of the product. For example, for PEG 400, n=8.2−9.1, and the molecular weight, which is to be understood herein as weight average molecular weight, would be about 400. A polyethylene glycol with an average molecular weight of about 400 is preferred in the practice of the invention due to its low volatility and ready availability. Polyethylene glycol 200 (n=4) and polyethylene glycol 300 (n=6) also are useful. Polyethylene glycol with a molecular weight above about 500 (n=11) can be used in addition to those of lower molecular weight, but they impart a waxy, hazy appearance to the applied coating when dried if present in substantial amounts. This tends to frustrate the purpose of a highlighting composition, but does not harm weld splatter inhibition. For a composition intended for the latter purpose, a PEG with a molecular weight of 6000 is most preferred for component (G).

The composition of the invention usually comprises low foaming nonionic surfactant, and, optionally, a low foaming amphoteric surfactant and/or a low or moderate foaming fluorosurfactant. Anionic surfactants can be utilized in the composition of the invention in lieu of nonionic surfactants. Sulfated or sulfonated anionic surfactants, when present in amounts above 2-5% by weight of the composition, can cause staining and etching of the metal surfaces and therefore should be avoided. However, other anionic surfactants, such as carboxylates and phosphates, can be used at high concentrations without staining or etching the metal surfaces. Nevertheless, component (B) is preferably selected from nonionic surfactants only. Examples of commercial surfactants useful for component (B) include TRITON ® CF-54 (modified polyethoxy adduct), TRITON ® DF12 (modified polyethoxylated linear alcohol), and TRITON ® DF-16 (a terminated ethoxylated linear alcohol), all products of Union Carbide Corporation; MAKON ® NF-12 (an alkylphenoxypolyoxyethylene alcohol) manufactured by Stepan Company; and PLURONIC ® L62 (a polyoxyethylene polyoxypropylene block copolymer) manufactured by BASF Wynadotte Corporation.

Amphoteric and ampholytic surfactants have been found to be highly preferred in those embodiments of the invention directed to hiliting. The hydrotroping (coupling) and wetting properties of the amphoteric and ampholytic surfactants make them particularly valuable. Typical useful amphoteric surfactants include the following commercially available products: MONATERIC ® CyNa50, a 50% active solution of the sodium salt of 2-caprylic-1-(ethyl beta oxypropionic acid)-imidazoline by Mona Industries, and ALKAWET ® LF, a proprietary amphoteric surfactant blend manufactured by Lonza.

Fluorosurfactants when present at low levels substantially enhance the wetting properties of the composition of the invention. The fluorosurfactants can be nonionic or anionic. Preferably the fluorosurfactant is a low to moderate foaming surfactant. Examples of useful commercially available fluorosurfactants include FLUOWET ® PL80, a mixture of perfluorinated phosphinic and phosphonic acids, and FLUOWET ® OTN, a fluoroaliphatic oxyethylate, products of Hoechst Celanese Corporation.

A composition of the invention should rapidly wet and form a foam-free film on the surface of the metal to which it is applied. Satisfactory highlighting performance has been observed with coatings having an areal density (mass per unit area) of from 0.1 to 100 grams per square meter (hereinafter often abbreviated as "g/m$^2$"). Normally, however, for either highlighting or prevention of weld splatter adhesion, an areal density within the range from 20-50 g/m$^2$ is preferred. Any surfactant combination can be used as long as the foam rapidly dissipates and the combination of surfactants does not contribute to staining and etching of the metal surface upon contact for extended periods.

Another requirement of a composition of the invention is that it must not cause or allow corrosion of the metal to which it is applied, at least during the period of contact with the metal. Red rust on ferrous metals and white rust on aluminum and zinc containing metal substrates prevent application of a suitable phosphate coating or subsequent organic coating (paint). In order to avoid such problems, the composition of the invention must contain a corrosion inhibitor. The preferred corrosion inhibitor comprises a combination of an alkali metal borate, preferably sodium or potassium borate and most preferably potassium borate, and a complex carboxylic acid. Ammonium borate is not desirable as a corrosion inhibitor in general purpose formulations of the invention because it causes staining of zinc and its alloys. An alkali metal borate is preferred in combination with an alkali metal, preferably sodium or potassium, neutralized complex carboxylic acid composition. The complex carboxylic acids preferably comprise, or more preferably consist of, a mixture of branched chain monocarboxylic acids and amino monocarboxylic acids. A suitable commercially available product to supply this part of the preferred corrosion inhibitor according to this invention is HOSTACOR ® TP-2291 from Hoechst Celanese Corporation.

The corrosion inhibitor most preferably is a combination of the borate and complex carboxylic acids. However, other corrosion inhibitors, such as sodium nitrite and alkanolamines such as ethanolamine, diethanolamine, triethanolamine and the like can be used. The combination of borate and complex carboxylate is preferred due to its lack of carcinogenic propensity and its mildness to the skin.

For ease of application, it is sometimes advantageous to adjust the rheological properties of a composition according to the invention. For example, vertically arranged surfaces may require a rather viscous composition in order to remain on the vertical surface for a sufficient length of time to permit any foam to dissipate and permit the visual inspection to be made. Known rheological modifying agents such as gums and cross-linked acrylic copolymers are useful in the practice of the invention. Preferred rheological modifying agents include ACCUSOL ® 810, a crosslinked acrylic copolymer product of Rohm and Haas Company, and xanthan gums such as KELZAN TM brand xanthan gum manufactured by Kelco Division of Merck and Company.

A working composition of the invention preferably has a pH in the range from 7 to 12, more preferably from 8 to 11, and still more preferably from 8.5 to about 10.5.

A preferred composition of the invention ready for application to metal for highlighting comprises, more preferably consists essentially of, or still more preferably consists of, water and:
(A) from 1.0 to 60% by weight of a polyethylene glycol with a molecular weight in the range from 200 to 500;
(B) from 0.5 to 15% by weight of low foaming unfluorinated nonionic surfactant;

(C) a corrosion inhibiting amount of a combination containing alkali metal borate and a neutralized mixture of complex carboxylic acids;

(D) from 0.3 to 10% by weight of low foaming unfluorinated amphoteric surfactant;

(E) from 0.001 to about 2% by weight of a fluorosurfactant; and (F) up to 1% by weight of a rheological property modifier and has a pH in the range from 7.5 to 11. In this composition or in any other composition according to this invention, component (D) preferably consists of (i) from 0.1 to 5.0, or more preferably from 0.3 to 3.0, % by weight of an alkali metal borate and (ii) from 0.05 to 5.0, or more preferably from 0.1 to 1.5, % by weight of salt of complex carboxylic acids, these percentages being referred to the entire working composition according to the invention.

A still more preferred hilite composition of the invention comprises, more preferably consists essentially of, or still more preferably consists of, water and:

(A) from 5 to 25% by weight of polyethylene glycol with a molecular weight of from 200 to 400;

(B) from 1 to 10% by weight of low foaming unfluorinated nonionic surfactant;

(C) from 0.3 to 3% by weight of potassium borate and from 0.1 to 1.5% by weight of alkali metal salts of complex carboxylic acids;

(D) from 1 to 7% by weight of low foaming unfluorinated amphoteric surfactant;

(E) from 0.05 to 0.5% by weight of fluorosurfactant; and (F) from 0.05 to about 0.6% of rheological modifier and has a pH in the range from 8.5 to 10.5.

The hiliter compositions as described above are also suitable for inhibiting the adherence of weld splatter in a process according to this invention. However, as already noted, for this particular purpose optional component (G) is preferably included in the composition. The ratio of the amount of component (G) to component (A) in a formulation for weld splatter adhesion inhibition preferably is in the range from 10:1 to 1:1, or more preferably in the range from 4.0:1.0 to 2.1:1.0.

It is preferred, in order to minimize adverse environmental impacts and/or the cost of preventing such adverse environmental impacts, that compositions according to the invention as defined above should be substantially free from certain ingredients, some of which have been used in compositions for similar purposes in the prior art. Specifically, it is increasingly preferred in the order given, independently for each preferably minimized component listed below, that these compositions, when directly contacted with metal in a process according to this invention, contain no more than 1.0, 0.35, 0.10, 0.08, 0.04, 0.02, 0.01, or 0.001 percent by weight of each of the following constituents: hexavalent chromium; divalent and higher than divalent metal cations; and any organic materials defined as VOC's by antipollution laws, including but not limited to, hydrocarbons and halohydrocarbons, alcohols, aldehydes, ketones, ethers, carboxylic acids, and esters having a vapor pressure in excess of 10 millibars at 25° C.

The practice of the invention can be further appreciated from the following nonlimiting examples.

EXAMPLE AND COMPARISON EXAMPLE
GROUP 1 -HIGHLIGHTING

A composition was prepared containing the following ingredients:

| Ingredient | % by Weight |
| --- | --- |
| PLURACOL ® E-400 (polyethylene glycol MW 400) | 20 |
| TRITON ® CF-54 (nonionic surfactant) | 3.7 |
| TRITON ® DF-12 (nonionic surfactant) | 0.5 |
| MONATERIC ® CyNa50 (Amphoteric surfactant) | 3.0 |
| FLUOWET ® PL-80 (Fluorosurfactant) | 0.1 |
| Potassium borate | 0.8 |
| HOSTACOR ® TP-2291 (Complex carboxylic acid mixture | 0.5 |
| ACCUSOL ® 810 (Acrylic Polymer rheology modifier) | 0.7 |
| Water | 70.7 | and the staining and etching properties of the composition were evaluated as follows. One panel each of cold rolled steel, electrogalvanized steel, and 5052 aluminum alloy were cleaned with acetone. One half of each panel was coated with the hilite composition by wiping the panel with an initially clean filter paper that had been saturated with the hilite composition. The panels were then exposed to the ambient conditions in a laboratory for 72 hours, simulating a weekend in a factory. The panels were rinsed with water and examined for staining and etching. No visual differences were detected between the coated and uncoated areas after 72 hours. No signs of darkening, staining or etching were observed.

Comparison hilite compositions were prepared as above except for deleting either the potassium borate or the HOSTACOR ®2291 from the composition. The hilite composition which contained HOSTACOR ®2291 but did not contain potassium borate produced staining on all zinc alloy coated panels. The hilite composition which contained the potassium borate but did not contain HOSTACOR 2291 produced oxidation on the steel panels coated with the composition after aging for 72 hours.

The performance of the hilite composition of the invention was compared to the performance of a commercially available aqueous hilite composition containing volatile organic compounds (P3 ®-Hilite-SG, a product of the Parker+Amchem Div. of Henkel Corp., which comprises butyl carbitol, nonionic surfactants, borax, triethanolamine and water. The gloss and uniformity of the hilite composition of the invention and the commercial hilite composition (P3 ®-Hilite-SG) were both excellent immediately after application. One hour after application the panel coated with the hilite composition of the invention continued to show excellent gloss while the gloss on the panel coated with the commercial hilite material was substantially reduced.

The coated panels were exposed to the ambient conditions in a laboratory for five days. There was no sign of red rust or white rust on any of the panels after the five days contact with the hilite compositions.

It can be seen from the examples that the hilite composition of the invention has advantageous properties over the commercially available material. The hilite composition of the invention contains no volatile organic compounds, retains its high gloss for a longer period than the commercial material and does not cause staining and etching of the metal substrate.

The commercially available hilite materials generally meet at least the minimum requirements for a hilite composition. The hilite composition of the present invention not only meets these requirements but in addition is water based and does not contain volatile organic compounds. The absence of volatile organic compounds permits use of the hilite composition of the invention without the need for compliance with all of the restrictions which accompany use of hilite compositions containing volatile organic compounds. A highlighting composition of the invention is an advance in the art because of the extended period over which the high gloss is maintained and the absence of volatile organic compounds as legally defined.

EXAMPLE AND COMPARISON EXAMPLE GROUP 2-INHIBITING WELD SPLATTER ADHESION

A preferred composition for inhibiting the adhesion of small bits of hot metal to a surface coated with the composition includes the following ingredients:

| Ingredient | Parts per Thousand by Weight |
| --- | --- |
| PEG 6000 | 60 |
| PEG 400 | 20 |
| ANTAROX ™ LF-330 (Low foaming modified linear aliphatic polyether from Rhône-Poulenc). | 10 |
| Boric acid | 2 |
| HOSTACOR ® TP-2291 | 2 |
| ACCUSOL ® 810 | 5 |
| MONATERIC ® CyNa50 | 5 |
| Aqueous 45% by weight potassium hydroxide solution | 2 |
| Triethanolamine | 8 |
| Deionized water | 886 |

This composition was applied to panels as in Group 1 (except that no aluminum panels were used), and panels so coated were welded together under conditions that would result in readily noticeable adhesion of weld spatter in the absence of any protective coating. No weld spatter was detected, and the coated panels were stored up to seven days in a normal laboratory atmosphere with no visible evidence of corrosion resulting. The composition has a water like viscosity, spreads easily on metals, and shows little to no sagging. Thus the use of the composition according to this invention for inhibiting the adhesion of hot metal is also an advance in the art.

What is claimed is:

1. A liquid composition which comprises water and:
    (A) from about 1.0 to about 60% by weight of polyethylene glycol having a weight average molecular weight in the range from 200 to 500:
    (B) from about 0.5 to about 15.0% by weight total of low foaming nonionic and non-staining anionic surfactant;
    (C) a corrosion inhibiting amount of corrosion inhibitor; and, optionally, at least one of:
    (D) from about 0.3 to about 10% by weight total of low foaming amphoteric surfactant;
    (E) from about 0.001 to about 2% by weight of a low or moderate foaming fluorosurfactant;
    (F) up to about 1% by weight of a rheology modifying agent; and
    (G) up to about 59% by weight, subject to the constraint that the total of components (A) and (G) does not exceed about 60% by weight, of polyethylene glycol having a weight average molecular weight of 600 or higher wherein low of moderate foaming is determined by the method wherein a glass stoppered 250 milliliter measuring cylinder, about 30 milliliters in diameter, is filled to the 150 milliliter mark with a 0.1% by weight solution in water at room temperature of the surfactant to be tested, the measuring cylinder is stoppered and then vigorously shaken for 30 seconds, the foam height immediately after shaking is measured, and the foam height is measured again 30 seconds after shaking is completed, a foam height of 60 milliliters or less after shaking of 30 milliliters of less after 30 seconds after shaking indicates a low foam surfactant, a foam height that does not indicate a low foam surfactant but is not more than 100 milliliters immediately after shaking of not more than 60 milliliters 30 seconds after shaking indicates a moderate foaming surfactant.

2. A composition according to claim 1, wherein component (C) includes (i) about 0.1 to about 5.0% by weight of an alkali metal borate and (ii) about 0.05 to about 5.0 % by weight of alkali metal salts of a mixture of branched chain monocarboxylic acids and amino monocarboxylic acids, the percentages being referred to the total composition, and component (B) is selected from nonionic surfactants.

3. A composition according to claim 2, where the alkali metal is potassium.

4. A composition according to claim 3 having a pH value within the range from about 7.5 to about 11 and not containing component (G).

5. A composition according to claim 4 having a pH value within the range from about 8.5 to about 10.5 and consisting essentially of water and:
    (A) from about 5 to about 25% by weight of polyethylene glycol with a molecular weight of from about 200 to about 400;
    (B) from about 1 to about 10% by weight of low foaming unfluorinated nonionic surfactant;
    (C) from about 0.3 to about 3% by weight of potassium borate and from about 0.1 to about 1.5% by weight of alkali metal salts of complex carboxylic acids;
    (D) from about 1 to about 7% by weight of low foaming unfluorinated amphoteric surfactant;
    (E) from about 0.05 to about 0.5% by weight of fluorosurfactant; and
    (F) from about 0.05 to about 0.6% of rheological modifier.

6. A composition according to claim 3 having a pH value within the range from about 8.5 to about 10.5 and consisting essentially of water and:
    (A) from about 5 to about 25% by weight of polyethylene glycol with a molecular weight of from about 200 to about 400;
    (B) from about 1 to about 10% by weight of low foaming unfluorinated nonionic surfactant;
    (C) from about 0.3 to about 3% by weight of potassium borate and from about 0.1 to about 1.5% by weight of alkali metal salts of complex carboxylic acids;
    (D) from about 1 to about 7% by weight of low foaming unfluorinated amphoteric surfactant;
    (E) from about 0.05 to about 0.5% by weight of fluorosurfactant; and (F) from about 0.05 to about 0.6% of rheological modifier.

7. A composition according to claim 3 comprising, as component (G), polyethyleneglycol having a molecular weight of about 4,000 to about 8,000 in an amount such that the ratio of component (G) to component (A) is in the range from about 4.0:1.0 to about 2.1:1.0.

8. A composition according to claim 2 having a pH value within the range from about 7.5 to about 11 and not containing component (G).

9. A composition according to claim 8 having a pH value within the range from about 8.5 to about 10.5 and consisting essentially of water and:
(A) from about 5 to about 25% by weight of polyethylene glycol with a molecular weight of from about 200 to about 400;
(B) from about 1 to about 10% by weight of low foaming unfluorinated nonionic surfactant;
(C) from about 0.3 to about 3% by weight of potassium borate and from about 0.1 to about 1.5% by weight of alkali metal salts of complex carboxylic acids;
(D) from about 1 to about 7% by weight of low foaming unfluorinated amphoteric surfactant;
(E) from about 0.05 to about 0.5% by weight of fluorosurfactant; and
(F) from about 0.05 to about 0.6% of rheological modifier.

10. A composition according to claim 2 having a pH value within the range from about 8.5 to about 10.5 and consisting essentially of water and:
(A) from about 5 to about 25% by weight of polyethylene glycol with a molecular weight of from about 200 to about 400;
(B) from about 1 to about 10% by weight of low foaming unfluorinated nonionic surfactant;
(C) from about 0.3 to about 3% by weight of potassium borate and from about 0.1 to about 1.5% by weight of alkali metal salts of complex carboxylic acids;
(D) from about 1 to about 7% by weight of low foaming unfluorinated amphoteric surfactant;
(E) from about 0.05 to about 0.5% by weight of fluorosurfactant; and
(F) from about 0.05 to about 0.6% of rheological modifier.

11. A composition according to claim 2 comprising, as component (G), polyethyleneglycol having a molecular weight of about 1,000 to about 10,000 in an amount such that the ratio of component (G) to component (A) is in the range from about 4.0:1.0 to 2.1:1.0.

12. A composition according to claim 1 having a pH value within the range from about 7.5 to about 11 and not containing component (G).

13. A composition according to claim 12 having a pH value within the range from about 8.5 to about 10.5 and consisting essentially of water and:
(A) from about 5 to about 25% by weight of polyethylene glycol with a molecular weight of from about 200 to about 400;
(B) from about 1 to about 10% by weight of low foaming unfluorinated nonionic surfactant;
(C) from about 0.3 to about 3% by weight of potassium borate and from about 0.1 to about 1.5% by weight of alkali metal salts of complex carboxylic acids;
(D) from about 1 to about 7% by weight of low foaming unfluorinated amphoteric surfactant;
(E) from about 0.05 to about 0.5% by weight of fluorosurfactant; and
(F) from about 0.05 to about 0.6% of rheological modifier.

14. A composition according to claim 1 having a pH value within the range from about 8.5 to about 10.5 and consisting essentially of water and:
(A) from about 5 to about 25% by weight of polyethylene glycol with a molecular weight of from about 200 to about 400;
(B) from about 1 to about 10% by weight of low foaming unfluorinated nonionic surfactant;
(C) from about 0.3 to about 3% by weight of potassium borate and from about 0.1 to about 1.5% by weight of alkali metal salts of complex carboxylic acids;
(D) from about 1 to about 7% by weight of low foaming unfluorinated amphoteric surfactant;
(E) from about 0.05 to about 0.5% by weight of fluorosurfactant; and
(F) from about 0.05 to about 0.6% of rheological modifier.

15. A composition according to claim 1 comprising, as component (G), polyethyleneglycol having a molecular weight of at least about 600 in an amount such that the ratio of component (G) to component (A) is in the range from about 10:1.0 to 1:1.

* * * * *